United States Patent

Wilson et al.

[11] 4,013,645
[45] Mar. 22, 1977

[54] FORMAMIDO CEPHALOSPORIN COMPOUNDS

[75] Inventors: Edward McKenzie Wilson, Hayes, England; Adrian Charles Ward Curran, Glascow, Scotland

[73] Assignee: Glaxo Laboratories Limited, Greenford, England

[22] Filed: Mar. 28, 1972

[21] Appl. No.: 238,992

Related U.S. Application Data

[63] Continuation of Ser. No. 874,039, Nov. 4, 1969, abandoned.

[30] Foreign Application Priority Data

Nov. 5, 1969    United Kingdom ............ 52438/68

[52] U.S. Cl. .......................... 260/243 C; 424/246
[51] Int. Cl.² ....................................... C07D 501/20
[58] Field of Search ............................... 260/243 C

[56] References Cited

UNITED STATES PATENTS 3,445,463  5/1969  Van Heyningen et al. .... 260/243 C
3,446,803  5/1969  Van Heyningen et al. .... 260/243 C

*Primary Examiner*—Nicholas S. Rizzo
*Attorney, Agent, or Firm*—Bacon & Thomas

[57] ABSTRACT

Protection of the amino group of a 7β-aminoceph-4-carboxylic acid or derivative thereof while at least one reaction is being carried out to introduce a desired group at at least one of the positions 1, 2, 3 and 4 by first converting the amino group to a formamido group and then regenerating the amino group after the desired group has been introduced. Novel intermediates may be produced which are compounds of the formula

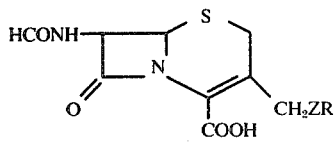

wherein R is $C_1$–$C_4$ alkyl and Z is —O—, —S—,

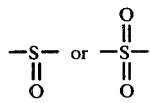

or salts or esters thereof.

3 Claims, No Drawings

FORMAMIDO CEPHALOSPORIN COMPOUNDS

This is a continuation of application Ser. No. 874,039, filed Nov. 4, 1969, now abandoned.

This invention is concerned with improvements in or relating to the production of analogues of cephalosporin C.

The cephalosporin compounds referred to in this specification are generally named with reference to the cepham ring structure. The cepham ring is represented as follows:

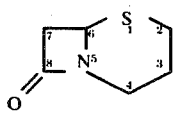

(I)

(see J.A.C.S. 1962, 84, 3400 and J.Chem.Soc. 1965, 5031) The term "cephem" referes to the basic cepham ring structure with a single double bond.

In the production of cephalosporin antibiotics and intermediates therefor it is frequently necessary to subject intermediates such as 3-acetoxymethyl-7β-aminoceph-3-em-4-carboxylic acid (commonly known as 7-aminocephalosporanic acid or 7-ACA) to a sequence of reactions to obtain the desired new compound. It may be undesirable to acylate the 7β-amino group with the desired acylating agent at an early stage of the synthesis. This may be because reactions which are effected elsewhere in the molecule, e.g. nucleophilic displacement reactions at the 3-position, will produce unwanted reactions at the newly introduced acyl group at the 7β-position. Furthermore if the 7β-amino group is left unprotected this may also be subject to unwanted reactions. We have now found that the 7β-amino group may be simply protected in an economic fashion by formylation while reactions are being effected elsewhere in the molecule and the 7β-formamido group may thereafter be readily decomposed to regenerate the 7β-amino group. Moreover the formamides do not normally appear to be subject to racemization as are similar systems in peptides. The formation of these 7β-formamido compounds is hence a highly useful technique in cephalosporin chemistry.

According to the invention therefore we provide a process for the preparation of a 7β-aminocephem-4-carboxylic acid or a derivative thereof which includes the steps of formylating a 7β-aminocephem-4-carboxylic acid or a derivative thereof having a group other than the desired group at the 1, 2, 3 or 4 position, effecting one or more reactions involving the 1, 2, 3 or 4 position, and N-deformylating the resulting compound to yield the desired 7β-aminocephem-4-carboxylic acid or derivative thereof.

The process according to the invention may involve a simultaneous reaction affecting more than one of said 1,2,3 or 4 positions or a sequence of two or more reactions affecting one or more of said positions.

The 7β-aminocephem-4-carboxylic acid or derivative thereof having a group other than the desired group at the 1,2,3 or 4 position may be a ceph-3-em or a ceph-2-em compound.

Formylation may be carried out by using any convenient formylating agent such as, for example, formic acid together with a lower alkanoic acid anhydride, e.g. acetic anhydride, e.g. at a temperature of up to 70° C preferably from 15° to 40° C. Alternatively formylation may be carried out with a formic acid ester, e.g. in refluxing ethyl formate with, if desired, a bifunctional catalyst such as pyrid-2-one or imidazole. Further alternative formylating agents are orthoformates e.g. lower alkyl orthoformates such as methyl or ethyl orthoformate. Other formylating agents include formyl halides e.g. formyl fluoride or formyl chloride; or formic acid, e.g. at 100° C.

The step of introducing the desired group at the 1, 2, 3 or 4 position may, for example, be an oxidation reaction at the 1-position to produce a sulphonyl or sulphoxide compound or, more commonly, a nucleophilic displacement reaction at the 3-position. Thus the invention provides a convenient method of effecting nucleophilic displacement of the 3-acetoxy group from 3-acetoxymethyl-7β-aminoceph-3-em-4-carboxylic acid. The invention also provides a convenient method of substituting the 3-hydroxymethyl group of 7β-amino-3-hydroxymethylceph-3-em-4-carboxylic acid.

Nucleophilic displacement reactions at the 3-position may be effected by any of the usual methods. Thus, for example, in starting from 7-ACA one may effect a direct displacement of the 3-substituent by reaction in a polar medium with the appropriate nucleophilic reagent. Alternatively, one may effect an indirect displacement by first converting the 7-ACA or corresponding 3-hydroxy compound into a compound having at the 3-position the group —CH$_2$X, X being a substituent readily replaceable by a nucleophile. The conditions for nucleophilic displacement reactions are described more fully in British Patent Specifications Nos. 912,541 and 1,012,943, in British Patent Application No. 38494/67. (Belgium Patent No. 719,711) and in U.S. Patent application Ser. No. 833,150 (Clark et al.)

Two important series of compounds which may be obtained by effecting nucleophilic displacement reactions at the 3-position are the 3-etherified and 3-thioetherified cephem-4-carboxylic acids and derivative thereof. Particularly important compounds in these series are those compounds wherein the substituent at the 3-position is a lower alkylthiomethyl group.

One may also effect esterification of the 4-carboxyl group while the 7β-amino group is protected using methods known in cephalosporin chemistry to affect such esterification. Esterification may be effected to provide ester residues of any desired alcohol or phenol e.g. of benzyl alcohols such as p-methoxybenzyl alcohol, di-p-methoxyphenylmethanol, triphenylmethanol, diphenylmethanol, benzoyloxymethanol or p-nitrobenzyl alcohol; furfuryl alcohol; t-butanol or 2,2,2-trichloroethanol.

N-Deformylation of the 7β-formamidocephem-4-carboxylic acid or derivative may be effected by any suitable technique for N-deacylating an acylamido group. Thus acid catalysed hydrolysis or alcoholysis of the 7β-formamido group may be effected with a mineral acid at a temperature of minus 15° to 100° C, preferably +15° to 40° C. A convenient reagent for the N-deformylation is concentrated hydrochloric acid in methanol or, preferably, in dioxan or tetrahydrofuran since undesirable transesterification reactions that tend to occur in methanol are thereby avoided.

The 7β-amino compound may be separated as an insoluble salt e.g. a hydrochloride or a hydrogen p-toluene sulphonate or it may be precipitated by adjustment of the pH (e.g. to an isoelectric point), if necessary with extraction with a suitable solvent.

Certain of the 7β-formamido compounds obtained as intermediates in the process of the invention are novel and an important class of such compounds are those having the formula:

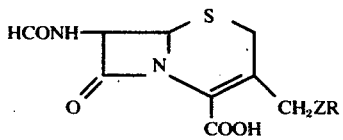

wherein R is an alkyl group containing 1–4 carbon atoms and X is —O—, —S—,

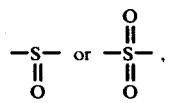

and salts and esters thereof.

In order that the invention may be well understood the following examples are given by way of illustration only. In the examples:

N.M.R. spectra were obtained at 60 MHz. The signs of the J value are not given.

Paper electrophoreses were carried out on Whatman No. 3 MM paper at pH 1.9 [98% formic acid (16.7 ml.), glacial acetic acid (84 ml.), acetone (105 ml.) and water (495 ml.)] at a potential drop of 25 volts/cm for 90 minutes.

The solvent systems utilized in the paper chromatography examinations are as follows:

System 1 ethyl acetate: n-butanol: 0.1M sodium acetate (pH 5.0) = 8:1:8, run downwards with the upper phase (in equilibrium with lower phase) as developing solvent, at 38° C, on Whatman No. 1 paper buffered to pH 5.0.

System 2 n-propanol: water = 7:3, run downwards at room temperature on Whatman No. 1 paper buffered with 0.1M-sodium acetate at pH 5.

System 3 comprises the upper phase of the system described below for thin-layer chromatography, run downwards on Whatman 3MM paper buffered to pH 6 with 0.05M-sodium dihydrogen phosphate.

Thin-layer chromatography (TLC) was carried out with layers of silica gel, with a solvent comprising the upper phase of the system n-butanol:ethanol:water = 4:1:5.

Chromatographic papers and plate were sprayed with potassium iodoplatinate and examined under ultraviolet light for absorbing and fluorescing spots. The presence of 7β-amino compounds in the chromatograms may be detected by spraying with ninhydrin since such compounds usually form a yellow colour.

"Petroleum spirit" is the fraction, b.p. 40°–60°.

Reaction mixtures were dried over dried magnesium sulphate and evaporated at 40° C at approx. 20 mm Hg, unless otherwise stated.

EXAMPLE 1

Preparation of 7β-amino-3-methylthiomethylceph-3-em-4-carboxylic acid

The title compound was prepared via the following reaction scheme (the steps are described in more detail below).

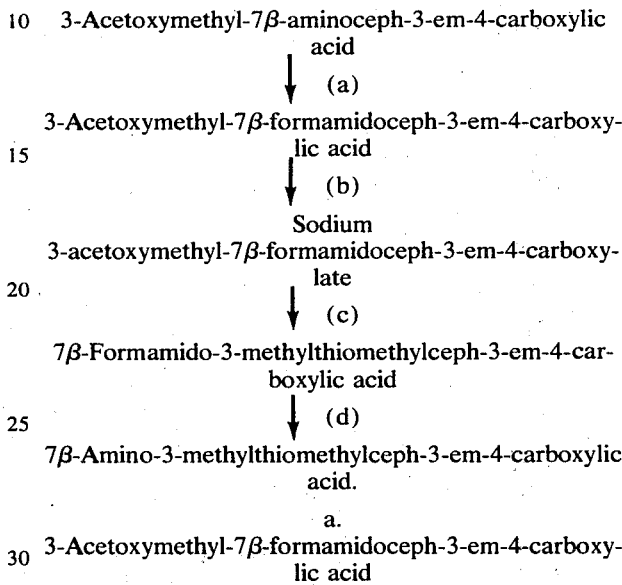

a. 3-Acetoxymethyl-7β-formamidoceph-3-em-4-carboxylic acid

3-Acetoxymethyl-7β-aminoceph-3-em-4-carboxylic acid (50.0 g) was dissolved in acetic anhydride (75 ml.) and formic acid (400 ml.) with stirring at 20° C. When complete solution was obtained (~ 5 min.) the solvents were evaporated (rotary evaporator, oil-pump), leaving a gum which was shaken with ethyl acetate (250 ml.). The insoluble material was removed by filtration and the filtrate was evaporated to dryness leaving a gum which was triturated under ether and petroleumether (b.p. 40°–60°), giving 3-acetoxymethyl-7β-formamidoceph-3-em-4-carboxylic acid as a pale yellow powder (43.6 g.), TLC $R_f$ 0.19, $[\alpha]_D^{20}$ + 113.5° (c 1.00, dioxan), λ max (pH6 buffer) 259 nm. (ε 8,400), $\nu_{max}$ (Nujol) 1772 (β-lactam) 1748 (acetate), 1708 (carboxylic acid), 1654, 1548 cm.$^{-1}$ (amide), τ (D$_2$O with NaHCO$_3$)1.67 (0.9-proton singlet: CHO), 1.75 (0.1-proton singlet: CHO), 4.20 (1-proton doublet, J 4.5 Hz.: C-7 H), 4.80 (1-proton doublet, J4.5 Hz.: C-6 H), 5.00, 5.26 [two 1-proton doublets (branches of a quartet), J 13 Hz: C-3 CH$_2$], 6.24 6.64 [two 1-proton doublets (branches of a quartet), J 18 Hz.: C-2 H$_2$] 7.86 (3-proton singlet: CH$_3$CO) (there is evidence for "cis" and "trans" forms in the secondary amide part).

b. Sodium 3-acetoxymethyl-7β-formamidoceph-3-em-4-carboxylate

3-Acetoxymethyl-7β-formamidoceph-3-em-4-carboxylic acid (10 g.) was stirred in acetone (120 ml.) for 10 min., the mixture filtered to remove a trace of solid and the filtrate treated with a 10% w/v solution of sodium 2-ethylhexanoate in acetone (60 ml.). After refrigeration for 1 hr. the precipitate was collected by filtration, washed with acetone and dried in vacuo giving sodium 3-acetoxymethyl-7β-formamidoceph-3-em-4-carboxylate as an off-white solid (10.0 g.), $[\alpha]_D^{20}$ + 121.3° (c. 1.00, water), $\lambda_{max}$ (water) 260 nm. (ε

8,600), $\nu_{max}$. (Nujol) 1760 (β-lactam), 1730 (acetate), 1672, 1544 (amide), 1600 cm.$^{-1}$ ($CO_2^-$).

c.
7β-Formamido-3-methylthiomethylceph-3-em-4-carboxylic acid

Sodium 3-acetoxymethyl-7β-formamidoceph-3-em-4-carboxylate (3.22 g., 0.01 mole) in water (50 ml.) was treated with methanethiol (1.44 g., 0.03 mole) in a sealed glass tube at 70° for 2 hr. The contents of the tube were transferred to an open vessel and stirred at room temperature for 15 min. to allow the excess thiol to evaporate off. The solution was covered with ethyl acetate (50 ml.) and the pH of the aqueous layer adjusted to 1. The ethyl acetate layer was collected and combined with further ethyl acetate extracts (2 × 50 ml.) of the aqueous layer. The combined extract was washed successively with water (50 ml.) and brine (50 ml.), dried, and the solution evaporated, leaving impure 7β-formamido-3-methylthiomethylceph-3-em-4-carboxylic acid as a colourless foam (2.22 g.), which was dissolved in acetone (12 ml.) and ether (12 ml.), and a 10% w/v solution of sodium 2-ethylhexanoate in acetone (12 ml.) was added. After refrigeration for 1 hr. the precipitate was collected by filtration, washed with acetone:ether (1:1, 2 × 10 ml.) and ether (2 × 20 ml.), and dried in vacuo giving sodium 7β-formamido-3-methylthiomethylceph-3-em-4-carboxylate as a colourless solid (1.69 g.), essentially homogeneous by thin-layer chromatography (trace of starting cephalosporanic acid), $[\alpha]_D^{20}$ + 75.5° (c 1.00, water), $\lambda_{max}$. (pH 6 buffer) 263 nm. (ε 7,760), $\nu_{max}$. (Nujol) 1760 (β-lactam), 1680, 1540 (amide), 1608 cm.$^{-1}$ ($CO_2^-$), τ($D_2O$) 1.78 (1-proton singlet, CHO), 4.31 (1-proton doublet, J 4.5 Hz.: C-7H), 4.84 (1-proton doublet, J 4.5 Hz.: C-6 H) 6.20, 6.65 [two 1-proton doublets (branches or a quartet) J 17 Hz.: C-2 H$_2$], 6.22, 6.69 [two 1-proton doublets (branches of a quartet), J 14 Hz.: C-3 CH$_2$], 7.98 (3-proton singlet; SCH$_3$)

The following in vitro biological results were obtained for the title compound: *Staph. aureus* 604 >2.5; *Staph. aureus* 663 2.5; *Staph. aureus* 3452 4; *Staph. aureus* 11127 4; *E. coli* 573 62; *S. typhimurium* 804 62; and *Pr. mirabilis* 431 125 [all by tube dilution assay (γ/ml)].

The mouse protection (ED$_{50}$ mg/kg/dose) against *Staph. aureus* 11127 (administered by sub-cutaneous injection) was 30. The % recovery of the compound from the urine of female rats following oral administration was 4.7.

7β-Amino-3-methylthiomethylceph-3-em-4-carboxylic acid and its hydrochloride d. (i) 7β-Formamido-3-methylthiomethylceph-3-em-4-carboxylic acid (2.88g) was dissolved in methanol (25 ml.) and the stirred solution was treated with concentrated hydrochloric acid (4.0 ml.). After 1.5 hr. at room temperature the solution was diluted with water (80 ml.) and washed with ethyl acetate (2 × 30 ml.) and ether (2 × 20 ml.), rotary evaporated to remove residual ether, and the pH adjusted to 3.5 with 0.880-ammonia. The precipitate was collected after overnight refrigeration, washed with water (2 × 10 ml), methanol (2 × 10 ml.) and ether (3 × 20 ml.), then dried giving 7β-amino-3-methylthiomethylceph-3-em-4-carboxylic acid as a colourless powder (1.41 g.), m.p. 222°–225° (decomp.), R$_f$0.60 (System 2), TLC R$_f$ 0.15, moves 2.0 cm. towards the cathode on electrophoresis at pH 1.9 (3-acetoxymethyl-7β-aminoceph-3-em-4-carboxylic acid moves 1.85 cm. under identical conditions), $\lambda_{max}$ (pH6 buffer) 266 nm. (ε 9,590), $\nu_{max}$. (Nujol) 1804 (β-lactam), 1536 cm.$^{-1}$ (carboxylate), τ($D_2O$ with NaHCO$_3$) 4.53 (~0.5-proton doublet, J 4.5 Hz.; C-7 H), 4.88 (1-proton doublet, J 4.5 Hz.; C-6 H), 5.21 (~0.5-proton doublet, J 4.5 Hz.; C-7 H), 6.14, 6.63 [two 1-proton doublets (branches of a quartet), J 18 Hz.; C-2 H$_2$], 6.21, 6.68 [two 1-proton doublets (branches of a quartet), J 14 Hz.; C-3 CH$_2$], 7.95 (3-proton singlet; SCH$_3$) [Found: C, 41.2; H, 4.6; N, 10.2; S, 23.6. C$_9$H$_{12}$N$_2$O$_3$S (260) requires C, 41.5; H, 4.6; N, 10.8; S, 24.6%].

(The low-field signal for the 7-proton indicates carbonation of the 7β-amino-group).

d. (ii) A solution of 7β-formamido-3-methylthiomethylceph-3-em-4-carboxylic acid (6.4 g.) in dioxan (50 ml.) was treated with 50% aqueous hydrochloric acid (7 ml.). After 2 hours at room temperature the mixture was freeze-dried. The resulting material was washed with ethyl acetate and ether, and dried to give 7β-amino-3-methylthiomethylceph-3-em-4-carboxylic acid, hydrochloride (5.95 g., 90%) as a white amorphous solid, $[\alpha]_D$ + 58.4° (C 1, 3% NaHCO$_3$), $\lambda_{max}$. (0.1 M pH 6 phosphate buffer) 265.5 nm. (ε 7,650), $\nu_{max}$. (Nujol) 1782 (β-lactam), 1715 and 1682 (carboxyl) cm$^{-1}$, τ ($D_2O$ - NaHCO$_3$) 6.59 (C-7 H 1-proton doublet, J 4.5 Hz) 6.91 (C-6 H 1-proton doublet, J 4.5 Hz), 6.2 and 6.67 [C-2 H$_2$ two 1-proton doublets (branches of a quartet), J 18 Hz], 6.24 and 6.7 [C-3 CH$_2$ two 1-proton doublets (branches of a quartet), J 13 Hz], and 7.98 (3-proton singlet, CH$_3$S).

EXAMPLE 2 a.
3-(3-Carbamoylpyridiniummethyl)-7β-formamidoceph-3-em-4-carboxylate

A solution of 3-acetoxymethyl-7β-formamidoceph-3-em-4-carboxylic acid (20 g., 0.06 mol.) and nicotinamide (29.3 g., 0.24 mol.) in water (300 ml.) was kept at 50° for 15 hrs. The cooled reaction mixture was filtered and the filtrate adsorbed onto a 60 cm. column of Deacidite FF ion-exchange resin. The column was eluted with distilled water and 100 ml. fractions collected. The optically active fractions were combined and freeze-dried, and the resultant solid slurried with acetone (3 × 100 ml.) to afford the required betaine as a white powder (7.1 g., 30%), R$_{PACA}$ 0.17 (system 2), R$_F$ 0.11 (electrophoresis, pH 1.9, 500 v, 2 hours), $[\alpha]_D$ −5° (C 1.00, water), $\lambda_{max}$. 262 nm (ε 10,300), $\nu_{max}$. (Nujol) 1770 cm$^{-1}$ (β-lactam), 1675 and 1528 cm$^{-1}$ (amide), and 1610 cm.$^{-1}$ ($CO_2^-$), τ($D_2O$) 0.31 to 2.0 (4-proton complex; pyridinium), 1.74 (0.9-proton singlet; CHO), 1.88 (0.1-proton singlet; CHO), 4.77 and 4.20 (two 1-proton doublets J = 4.5 Hz.; 6- and 7-H), 4.38 and 4.50 [two 1-proton doublets (branches of a quartet, J = 14 Hz., 3-CH$_2$),] 6.36 and 6.79 [two 1-proton doublets (branches of a quartet) J = 18 Hz., 2-H] (Found: C, 48.3; H, 4.5; N, 15.7; S, 6.9. C$_{15}$H$_{14}$N$_4$SO$_5$ requires C, 49.7; H, 3.9; N, 15.5; S, 8.8%).

b.
7β-Amino-3-(3-carbamoylpyridiniummethyl)ceph-3-em-4-carboxylate bis-hydrochloride 3-(3-Carbamoylpyridiniummethyl)7β-formamidoceph-3-em-4-carboxylate (2 g.) was added portionwise to a stirred mixture of concentrated hydrochloric acid (3 ml.) and methanol (40 ml.), giving an orange solution which was stirred for 4 hours at room temperature. the reaction mixture was diluted with ethyl acetate (150 ml.) and the precipitated solid collected by filtration giving the title compound as an off-white powder (1.13 gm., 48%), $R_{PACA}$ 0.09 (system 2), $R_F$ 0.4 (electrophoresis, pH 1.9, 500 v, 90 min.), $[\alpha]_D$ −65° (C 1.00, water), $\lambda_{max}$ 263 nm ($\epsilon$ 8,400), $\nu_{max}$ (Nujol) 1780 cm.$^{-1}$ ($\beta$-lactam), 1687 (CONH), and 2600 cm.$^{-1}$ ($NH_3^+$), 1687 cm.$^{-1}$ (—$CO_2H$). $\tau$ ($D_2O$) 0.3–1.8 (pyridinium protons), 4.02 and 4.48 [two 1-proton doublets (branches of a quartet) J = 18 Hz, 3-$CH_2$], 6.11 and 6.56 [two 1-proton doublets (branches of a quartet) J = 17 Hz., 2-H], and 4.54 and 4.69 (two 1-proton doublets, J = 4.5 Hz., 6- and 7-H). (Found: C, 36.7; H, 4.3; N, 13.5; S, 6.2; Cl, 19.6. $C_{14}H_{16}N_4SO_4Cl_2$ requires C, 41.2; H, 3.9; N, 13.9; S, 7.9; Cl, 17.5%).

EXAMPLE 3 a. 3-(4-Carbamoylpyridiniummethyl)-7β-formamidoceph-3-em-4-carboxylate

3-Acetoxymethyl-7β-formamidoceph-3-em-4-carboxylic acid (20.0 g.) and isonicotinamide (29.3 g.) were dissolved in water (300 ml.) and kept at 50° for 15 hours. The cooled reaction mixture was filtered, passed through a Deacidite FF ion-exchange resin-column (60 cm.) and the column elated with distilled water. The combined optically-active fractions were freeze-dried, and the resultant solid slurried with acetone (3 × 100 ml.) giving the title compound as a white powder (7.2 g., 25%), $R_{PACA}$ 0.18 (system 2), $R_F$ 0.15 (electrophoresis, pH 1.9, 500 v, 2 hours). $[\alpha]_D$ − 5° (C 1.00, water), $\lambda_{max}$. 262 nm ($\epsilon$ 13,000), $\nu_{max}$. (Nujol) 1770 cm.$^{-1}$ ($\beta$-lactam), 1675 and 1528 cm.$^{-1}$ (CONH) and 1610 cm.$^{-1}$ ($CO_2^-$), $\tau$ ($D_2O$) 1.73 (0.9-proton singlet, CHO), 1.88 (0.1-proton singlet, CHO), 0.82 to 1.57 (4-proton complex; pyridinium), 4.19 and 4.75 (two 1-proton doublets, J 4.5 Hz., 6- and 7-H), 4.26 and 4.58 [two 1-proton doublets (branches of quartet), J 14 Hz., 3-$CH_2$], 6.25 and 6.79 [two 1-proton doublets (branches of a quartet) J = 18 Hz., 2-H]. (Found: C, 44.1; H, 4.2; N, 14.9; S, 7.1. $C_{15}H_{14}N_4SO_5.2H_2O$ requires C, 45.2; H, 4.6; N, 14.1; S, 8.1%).

b. 7β-Amino-3-(4-carbamoylpyridiniummethyl)ceph-3-em-4-carboxylate bishydrochloride 3-(4-Carbamoylpyridiniummethyl)-7β-formamidoceph-3-em-4-carboxylate (1 g.) was added to a mixture of methanol (20 ml.) and concentrated hydrochloric acid (2 ml.), giving a pale yellow solution. After 10 minutes a white solid precipitated and the suspension was stirred for 4 hours at room temperature. The solid was collected by filtration giving the title compound as a white powder (600 mg.). [A second, less pure, crop was isolated by diluting the filtrate with ethyl acetate], $R_F$ 0.4 (electrophoresis, pH 1.9, 500 v, 90 min.) $R_{PACA}$ 0.08 (system 2), $[\alpha]_D$ − 35° (c 1.00, water), $\lambda_{max}$. 263 nm. (c 9,400), $\nu_{max}$. (Nujol) 1780 cm.$^{-1}$ ($\beta$-lactam), 1687 cm.$^{-1}$ (CONH), 1687 ($CO_2H$), and 2600 cm.$^{-1}$ ($NH_3+$), $\tau$ ($D_2O$) 0.74–1.48 (pyridinium protons), 4.04, 4.47 [two 1-proton doublets (branches of a quartet), J = 14 Hz., 3-$CH_2$], 4.54 and 4.69 [two 1-proton doublets, J = 4.5 Hz., 6- and 7-H], 6.11 and 6.56 [two 1-proton doublets (branches of a quartet) J = 17 Hz., 2-H]. (Found C, 37.2; H, 4.3; N, 13.5; S, 6.2; Cl, 19.6 $C_{14}H_{16}N_4SO_4Cl_2$ requires C, 41.3; H, 3.9; N, 13.9; S, 7.9; Cl, 17.5%).

EXAMPLE 4 a. Diphenylmethyl 7β-formamido-3-methylthiomethylceph-3-em-4-carboxylate

A solution of sodium 7β-formamido-3-methylthiomethylceph-3-em-4-carboxylate (6.20 g., 0.02 mole) in water (50 ml.) was covered with ethyl acetate (50 ml.) and the pH adjusted to 2.5 (2N-hydrochloric acid). The ethyl acetate layer was collected, combined with further ethyl acetate extracts (2 × 50 ml.), washed with water (50 ml.) and brine (50 ml.), dried (magnesium sulphate), and the solvent evaporated, leaving a foam which was dissolved in tetrahydrofuran (250 ml.) and treated with diphenyldiazomethane (3.88 g., 0.02 mole) in petrol (b.p. 60°–80°; 70 ml.). The solution was kept in the dark overnight, a small amount of glacial acetic acid was added to destroy unreacted diphenyldiazomethane, and the volume of the solution reduced to 30 ml., then diluted with ethyl acetate (200 ml.) This dilute solution was washed with 3%-sodium bicarbonate (5 × 100 ml.) water (2 × 100 ml.), and brine (100 ml.), dried (magnesium sulphate), and the solvent evaporated, leaving an orange oil (7.22g), TLC (benzene;ethyl acetate×2:1 as developing solvent) $R_F$ 0.62, 0.80 (trace), 0.95. This oil was dissolved in benzene (80 ml.), and petrol (b.p. 40°–60°; 250 ml.) was added, precipitating a gum which was triturated under petrol giving diphenylmethyl 7β-formamido-3-methylthiomethylceph-3-em-4-carboxylate as a fawn powder (3.02 g.), TLC $R_F$ 0.62, m.p. 60°–65°, $[\alpha]_D$−24.5° (c 1.00, dioxan), $\lambda_{max}$. (ethanol) 268 nm. ($\epsilon$ 7,000), $\nu_{max}$. ($CHBr_3$) 1780 ($\beta$-lactam), 1712 (ester), 1690, 1498 cm.$^{-1}$ (CONH), $\tau$ ($CDCl_3$) 1.68 (1-proton singlet; CHO), 2.58 (10-proton singlet; aromatic protons), 2.98 (1-proton singlet; $Ph_2CH$), 3.32 (1-proton doublet, J 9 Hz.; CONH), 4.08 (1-proton double doublet, J 5, 9 Hz.; C-7 H), 4.92 (1-proton doublet, J 5 Hz.; C-6 H), 6.29, 6.56 [two 1-proton doublets (branches of a quartet), J 14 Hz., C-3 $CH_2$], 6.42 (2-proton singlet; C-2 $H_2$), 8.11 (3-proton singlet; $CH_3S$). [Found C, 61.6; H, 5.3; N, 5.5; S, 13.5. $C_{23}H_{22}N_2O_4S_2$ (454.6) requires C, 60.9, H, 4.9; N, 6.2; S, 14.1%].

b. Diphenylmethyl 7β-amino-3-methylthiomethylceph-3-em-4-carboxylate

Diphenylmethyl 7β-formamido-3-methylthiomethylceph-3-em-4-carboxylate (0.88g., 0.0019 mole) in methanol (10 ml.) was treated dropwise with concentrated hydrochloric acid (1.0ml.). A colourless precipitate separated immediately but after 5 min. stirring this dissolved. However, after 15 min. a second precipitate came down, and after the mixture was refrigerated for 2 hr., the solid was harvested by filtration, washed with a little water, then dried over phosphorus pentoxide. The dried solid was stirred with ethyl acetate (15 ml. for 2 hr., × 2) to leach out unchanged starting material, the remaining solid was collected by filtration, washed with ether and dried, giving diphenylmethyl 7β-amino-3-methylthiomethylceph-3-em-4-carboxylate hydrochloride (0.35 g.), TLC $R_F$ 0.83. [Found: Cl (ionic), 7.6. $C_{22}H_{23}N_2O_3S_2Cl$ (463.0) requires Cl, 7.7%]. A portion (0.33g.) of this hydrochloride was stirred in a mixture of 3%-sodium bicarbonate (30 ml.) and ethyl acetate (30 ml.) until it dissolved (2 hr.). The ethyl acetate layer was collected and combined with a further ethyl acetate extract (25 ml.) of the aqueous layer, the combined extract washed with water (30 ml.), dried (magnesium sulphate), and the solvent evaporated, leaving an oil which solidified, giving diphenylmethyl 7β-amino-3-methylthiomethylceph-3-em-4-carboxylate (0.28 g.), TLC $R_f$ 0.83, m.p. 119°–123° $[\alpha]_D$ –81.4° (c 1.00, dioxan), $\lambda_{max}$ (ethanol) 270 nm. ($\epsilon$ 7,130), $\nu_{max}$. (CHBr$_3$) 3390, 3320 (NH$_2$), 1768 (β-lactam), 1712 cm.$^{-1}$ (ester), τ (CDCl$_3$) 2.86 (10-proton singlet; aromatic protons), 3.05 (1-proton singlet; Ph$_2$CH), 5.03 (1-proton doublet, J 5 Hz.; C-6 H), 5.29 (1-proton broad doublet, J 5 Hz.; C-7 H), 6.37, 6.67 [two 1-proton doublets (branches of a quartet), J 13.5 Hz.; C-3 CH$_2$], 6.45 (2-proton singlet; C-2 H$_2$), 8.16 (3-proton singlet; SCH$_3$), 8.22 (2-proton broad singlet, NH$_2$). A portion (0.200 g., 0.0005 mole) of this amine was dissolved in ethyl acetate (4 ml.) and ether (2 ml.) and a solution of p-toluenesulphonic acid monohydrate (0.089g., 0.0005mole) was added. The precipitate was collected by filtration, washed with ethyl acetate: ether=1:1, and dried giving diphenylmethyl 7β-amino-3-methylthiomethylceph-3-em-4-carboxylate, hydrogen p-toluenesulphonate as a colourless powder (0.126 g.), m.p. 159°–161° (decomp), $[\alpha]_D$ –33.2° (c 1.00, dimethylacetamide), $\lambda_{max}$. (ethanol) 264 nm. ($\epsilon$ 7,560), $\nu_{max}$. (CHBr$_3$) ~ 2600 (NH$_3$), 1785 (β-lactam), 1720 (ester), 1005 cm.$^{-1}$ (SO$_3^-$), τ (CDCl$_3$ with DMSO d-6) 1.6–2.3 (3-proton singlet; NH$_3$), 2.23, 2.90 [two-proton doublets (branches of a quartet), J 9 Hz.; p-disubstituted aromatic protons], 2.70 (10-proton singlet; aromatic protons) 3.11 (1-proton singlet; Ph$_2$CH), 4.88, 4.98 (2 two 1-proton doublets, J 5 Hz.; C-6 H, C-7 H), 6.14, 6.47 [two 1-proton doublets (branches of a quartet), J 13.5 Hz.; C-3 CH$_2$], 6.30, 6.85 [two 1-proton doublets (branches of a quartet), J 16 Hz,: C-2 H$_2$] 7.68 (3-proton singlet; CH$_3$C$\leqslant$), 8.16 (3-proton singlet; CH$_3$S). [Found: C, 58.7; H, 5.0; N, 4.3; S, 15.6. C$_{29}$H$_{30}$N$_2$O$_6$S$_3$ (598.8) requires C, 58.5; H, 5.0; N, 4.7; S, 16.0%].

EXAMPLE 5

Diphenylmethyl 7β-amino-3-methylthiomethylceph-3-em-4-carboxylate hydrochloride

A solution of 7β-formamido-3-methylthiomethylceph-3-em-4-carboxylic acid (4.8 g.; 16.7 mmole) on peroxide-free dioxan (50 ml.) was added to a solution of diphenyldiazomethane (from 8.4 g. benzophenone hydrazone: 43 mmole) in ether (150 ml.). The solution was allowed to stand at room temperature overnight, then treated with glacial acetic acid (2.5 ml.), and evaporated to give a pale yellow oil which was shown by TLC to consist of two major components. The oil was taken up in ether (100 ml.) washed, with saturated sodium hydrogen carbonate solution (50 ml.), 2N-hydrochloric acid (50 ml.), and saturated brine (50 ml.). The solution was dried (sodium sulphate) and evaporated to give an oil which was used directly in the deformylation experiment. Thin-layer chromatography (benzene:ethyl acetate = 2:1, Merck's silica) revealed two major components corresponding to a product from decomposition of excess diphenyl-diazomethane, and diphenylmethyl 7β-formamido-3-methylthiomethylceph-3-em-4-carboxylate.

The oil was digested in a mixture of peroxide-free tetrahydrofuran (120 ml.) and concentrated hydrochloric acid (30 ml.), and stirred at room temperature until thin-layer examination revealed that no diphenylmethyl 7β-formamido-3-methylthiomethylceph-3-em-4-carboxylate remained. This occurred after ~5 hours, during which time the hydrochloride salt crystallised out. The solution was refrigerated overnight, filtered, and the solid dried to give diphenylmethyl 7β-amino-3-methylthiomethylceph-3-em-4-carboxlate, hydrochloride (2.4 g.), m.p. 185°–192° (decomp.), $\lambda_{max}$. (EtOH) 265 nm. ($\epsilon$ 6,850), $[\alpha]_D$ – 24.9° (C 1.0, DMSO), $\nu_{max}$. (Nujol) 2620 (—N$^+$H$_3$), 1770 (β-lactam), 1711 (ester), and 702 cm$^{-1}$ (phenyl), τ (DMSO-d$_6$) 8.1 (3-proton singlet; —S—CH$_3$), 6.25 (2-proton singlet; C-2 protons), 6.05, 6.35 (two 1-proton doublets, J = 18 Hz; 3-CH$_2$—S—), 4.70 (1-proton doublet, J = 5 Hz; 7-H), 4.5 (1-proton doublet, J = 5 Hz; 6-H), 2.9 (1-proton singlet; CHPh$_2$), 2.45 (10-proton multiplet; aromatic protons). (Found: C, 57.3; H, 5.0; Cl, 7.9; N, 5.8; S, 13.1. C$_{22}$H$_{23}$ClN$_2$O$_3$S$_2$ requires C, 57.2; H, 5.0; Cl, 7.7; N, 6.0; S, 13.8%).

Concentration of the mother liquor from the deformylation experiment and trituration with ether gave a further crop of the hydrochloride (2.1 g.), identical with material obtained as described above. The total yield of diphenylmethyl 7β-amino-3-methylthiomethylceph-3-em-4-carboxylate, hydrochloride was 4.5 g. (60% based on 7β-formamido-3-methylthiomethylceph-3-em-4-carboxylic acid). The same compound was also obtained, in 38% yield, by performing the deformylation in dioxan containing 6N-hydrochloric acid.

EXAMPLE 6 a.

3-Acetoxymethyl-7β-formamidoceph-2-em-4α-carboxylic acid

3-Acetoxymethyl-7β-formamidoceph-3-em-4-carboxylic acid (3.0 g., 1 mmol.) was suspended in dry pyridine (12 ml) at room temperature. Acetic anhydride (1.2 ml.) was added to the stirred suspension and the reaction allowed to proceed for 1 hr. On cooling with ice, the pyridinium salt crystallised and this was filtered off. Treatment of the solid with dilute hydrochloric acid and extraction with ethyl acetate gave the free acid which was obtained as a gum after washing the organic phase with water, drying, and evaporation. The gum (0.61 g 20.3%) could not be crystallised. The spectroscopic properties of the product are consistent with the structure of the compound named in the title $\nu_{max}$ (film) 3300 (NH), 1770 (β-lactam), 1730 (OCOCH$_3$), 1675 cm$^{-1}$ (HCON—) τ (D$_2$O/NaHCO$_3$) 1.82 (singlet, HCO—), 3.52 (singlet, =CH—S), 4.51 and 4.71 (double doublet, J=4 Hz, 6H and 7H protons), 5.22 (collapsed quartet), 5.82 (singlet, CHCO$_2$H) and 7.89 (singlet, CH$_3$COO—).

b.

3-Acetoxymethyl-7β-aminoceph-2-em-4α-carboxylic acid

3-Acetoxymethyl-7β-formamidoceph-2-em-4α-carboxylic acid (1.5 g, 0.5 mmol) was dissolved in dioxan (12 ml) containing 50% conc. hydrochloric acid (1.7 ml.) at room temperature. After 2 hr. the excess solvent was removed by freeze-drying to give solid hydrochloride (1.5 g., 100%). Adjustment of the pH to the isoelectric point with a dilute ammonia solution failed to give a precipitate of the zwitterion. The infrared and n.m.r. results on the freeze-dried solution were consistant with the structure of the compound named in the title. Paper electrophoresis was carried out on Whatman No. 1 paper at pH 1.9 [98% formic acid (16.7 ml), glacial acetic acid (84 ml.), acetone (105 ml) and water (495 ml)] at a potential drop of 125 volts/cm for 20 min. The mobility obtained was 5 cm as compared with 3-acetoxymethyl-7β-aminoceph-3-em-4-carboxylic acid which has a mobility of 3.5 cm.

c. Sodium 3-acetoxymethyl-7β-(2,6-dichlorobenzamido)ceph-2-em-4α-carboxylate The hydrochloride of 3-acetoxymethyl-7β-aminoceph-2-em-4α-carboxylic acid (1.5 g., 0.05 m.mol) was heated in refluxing dry chloroform (20 ml) containing hexamethyldisilazane (3.2 ml. 0.015 mol) for 1 hr. The excess silylating reagent and solvent were removed under high vacuum. The resulting gum was redissolved in dry ethyl acetate (20 ml) and 2,6-dichlorobenzoyl chloride (1.0 g 0.45 mmol) added. the reaction was carried out for 1 hr. at reflux. Treatment of the organic phase with dilute hydrochloric acid, water, drying and evaporation gave a gum. Addition of a solution of 10% sodium 2-ethylhexanoate in ethyl acetate precipitated a sodium salt, $\nu_{max}$ (Nujol) 3300 (NH), 1760 (β-lactam), 1720 (acetate), 1660 (amide) and 1605 cm$^{-1}$ (—CO$_2$Na), R$_F$ (system 3) 0.53 (with an impurity, R$_F$ 0.19). These properties are consistent with the structure of the compound named in the title.

We claim:
1. A compound of the formula:

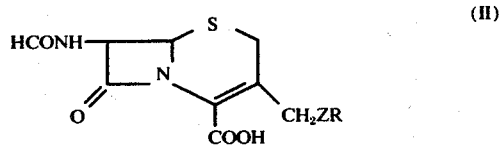

(II)

wherein R is an alkyl group containing 1–4 carbon atoms and Z is —O—, —S—,

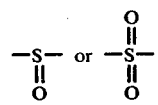

or a slat or ester thereof.

2. A compound as claimed in claim 1 being 7β-formamido-3-methylthiomethylceph-3-em-4-carboxylic acid.

3. A compound as claimed in claim 1 being diphenylmethyl 7β-formamido-3-methylthiomethylceph-3-em-4-carboxylate.

* * * * *